US009352081B2

(12) United States Patent
Munro et al.

(10) Patent No.: US 9,352,081 B2
(45) Date of Patent: May 31, 2016

(54) DRIP CHAMBER WITH HYDROPHOBIC INTERIOR SURFACE

(71) Applicant: Baxter Healthcare SA, Glattpark (CH)

(72) Inventors: James F. Munro, Ontario, NY (US); Tuan Bui, Buffalo, NY (US)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 517 days.

(21) Appl. No.: 13/828,859

(22) Filed: Mar. 14, 2013

(65) Prior Publication Data

US 2014/0276457 A1    Sep. 18, 2014

(51) Int. Cl.
*A61M 5/14* (2006.01)
*A61M 5/168* (2006.01)

(52) U.S. Cl.
CPC ........... *A61M 5/1411* (2013.01); *A61M 5/1689* (2013.01); *Y10T 29/49826* (2015.01)

(58) Field of Classification Search
CPC .............. A61M 5/1411; A61M 5/1689; Y10T 29/49826
USPC .................................................. 604/251–255
See application file for complete search history.

(56) References Cited

U.S. PATENT DOCUMENTS

| | | |
|---|---|---|
| 4,321,461 A | 3/1982 | Walter, Jr. et al. |
| 4,328,801 A | 5/1982 | Marx et al. |
| 4,449,534 A * | 5/1984 | Leibinsohn Saul . A61M 5/1689 604/251 |
| 4,490,140 A | 12/1984 | Carr et al. |
| 4,504,263 A | 3/1985 | Steuer et al. |
| 4,525,163 A | 6/1985 | Slavik et al. |
| 4,583,975 A | 4/1986 | Pekkarinen et al. |
| 4,634,426 A | 1/1987 | Kamen |
| 4,820,281 A | 4/1989 | Lawler, Jr. |
| 4,909,786 A | 3/1990 | Giiselhart et al. |
| 4,936,828 A | 6/1990 | Chiang |
| 5,045,069 A | 9/1991 | Imparato |
| 5,057,090 A | 10/1991 | Bessman |
| 5,415,641 A | 5/1995 | Yerlikava et al. |
| 5,562,615 A | 10/1996 | Nassif |
| 5,899,665 A | 5/1999 | Makino et al. |
| 6,049,381 A | 4/2000 | Reinties et al. |
| 6,083,206 A | 7/2000 | Molko |
| 6,149,631 A | 11/2000 | Havdel, Jr. |
| 6,159,186 A | 12/2000 | Wickham et al. |
| 6,562,012 B1 | 5/2003 | Brown et al. |

(Continued)

FOREIGN PATENT DOCUMENTS

| | | |
|---|---|---|
| WO | WO 02/40084 | 5/2002 |
| WO | WO 2009/039203 | 3/2009 |
| WO | 2012104779 | 8/2012 |

*Primary Examiner* — Manuel Mendez

(74) *Attorney, Agent, or Firm* — Greer, Burns & Crain, Ltd.

(57) ABSTRACT

A drip chamber for an infusion tube, including: a first end including a drip tube; a second end including an exit port; and a wall connecting the first and second ends and including an interior surface with a hydrophobic portion. The drip chamber includes a space enclosed by the interior wall and the first and second ends. The hydrophobic portion of the interior surface repels liquid contacting the hydrophobic coating. The hydrophobic portion of the interior surface enables light to refract through the hydrophobic portion and the wall in the same manner as is the case when the hydrophobic portion is not present on the interior surface.

11 Claims, 3 Drawing Sheets

(56) References Cited

U.S. PATENT DOCUMENTS

| | | |
|---|---|---|
| 6,736,801 B1 | 5/2004 | Gallagher |
| 6,984,052 B1 | 1/2006 | Del Castillo |
| 7,190,275 B2 | 3/2007 | Goldberg et al. |
| 7,479,128 B1 * | 1/2009 | Lenz .................... A61L 29/085 604/265 |
| 7,695,448 B2 | 4/2010 | Cassidy et al. |
| 7,767,991 B2 | 8/2010 | Sacchetti |
| 7,892,204 B2 | 2/2011 | Kraus |
| 7,918,834 B2 | 4/2011 | Mernoe et al. |
| 2003/0006159 A1 * | 1/2003 | Thorball .................... A23L 2/52 206/438 |
| 2003/0045840 A1 | 3/2003 | Burko |
| 2006/0291211 A1 | 12/2006 | Rodriguez et al. |
| 2008/0004574 A1 | 1/2008 | Dyar et al. |
| 2008/0051732 A1 | 2/2008 | Chen |
| 2010/0217229 A1 | 8/2010 | Miner |
| 2010/0309005 A1 | 12/2010 | Warner et al. |
| 2012/0013735 A1 | 1/2012 | Tao |

* cited by examiner

DRIP CHAMBER WITH HYDROPHOBIC INTERIOR SURFACE

TECHNICAL FIELD

The present disclosure relates to a drip chamber, for an infusion tube, with an interior surface having a hydrophobic surface, in particular, a hydrophobic surface with optical properties enabling optical imaging through the hydrophobic surface.

BACKGROUND

FIG. 5 is a pictorial representation of prior art drip chamber 200 with spurious droplets 202 clinging to interior surface 204 of the drip chamber. For purposes of illustration, FIG. 5 is presented as a line drawing. During operation of drip chamber 200, when fluids are flowing through the drip chamber, droplets of fluid, such as droplets 202, form on the interior surface of the drip chamber due to splashing of the fluid, or by evaporation of the fluid from the reservoir at the bottom of the drip chamber and subsequent condensation of the fluid on the interior surface. Droplets 202 can cause substantial problems with respect to imaging the drip chamber, for example, imaging drop 206 pendant from drip tube 208. For example, the droplets can cause errors in the measurement of the size of drop 206. Droplets such as droplets 202 in other portions of the drip tube, for example in the vicinity of a meniscus, can cause similar problems, such as errors in measuring a position/level of the meniscus.

SUMMARY

According to aspects illustrated herein, there is provided a drip chamber for an infusion tube, including: a first end including a drip tube; a second end including an exit port; and a wall connecting the first and second ends and including an interior surface with a hydrophobic portion. The drip chamber includes a space enclosed by the interior wall and the first and second ends. The hydrophobic portion of the interior surface repels liquid contacting the hydrophobic coating. The hydrophobic portion of the interior surface enables light to refract through the hydrophobic portion and the wall in the same manner as is the case when the hydrophobic portion is not present on the interior surface.

According to aspects illustrated herein, there is provided a method of fabricating a drip chamber for an infusion tube, including: forming a first end including a drip tube; forming a second end including an exit port; forming a wall connecting the first and second ends and including an interior surface; forming a hydrophobic portion on the interior surface; and enclosing a space with the interior surface and the first and second ends. The hydrophobic portion of the interior surface repels liquid contacting the hydrophobic coating. The hydrophobic portion of the interior surface enables light to refract through the hydrophobic portion and the wall in the same manner as is the case when the hydrophobic portion is not present on the interior surface.

According to aspects illustrated herein, there is provided an optical imaging system for an infusion tube, including: a drip chamber with: a first portion with a drip tube; a second portion with an exit port; a third portion located between the first and second portions; and a wall connecting the first and second ends and including an interior surface with a portion having a hydrophobic portion of the interior surface aligned with at least one of the first or third portions in a direction orthogonal to a longitudinal axis for the drip chamber passing through the first and second ends. The system includes: at least one light source for emitting light; and an optics system including at least one lens for receiving and transmitting the light transmitted through the hydrophobic portion of the interior surface and the at least one of the first or third portions, and an image sensor for receiving the transmitted light from the at least one lens and generating and transmitting data characterizing the transmitted light from the at least one lens. The system includes a memory element configured to store computer readable instructions and at least one specially programmed processor configured to execute the computer readable instructions to generate, using the data, at least one image of the at least one of the first or third portions. The hydrophobic portion of the interior surface repels liquid contacting the hydrophobic portion of the interior surface. The hydrophobic portion of the interior surface enables the light to pass through the hydrophobic portion of the interior surface without scattering.

According to aspects illustrated herein, there is provided a method of imaging an infusion tube having a drip chamber including a first portion with a drip tube, a second portion with an exit port, a third portion located between the first and second portions, and a wall connecting the first and second ends and including an interior surface with a portion having a hydrophobic portion of the interior surface aligned with at least one of the first or third portions in a direction orthogonal to a longitudinal axis for the drip chamber passing through the first and second ends, the method includes: repelling liquid contacting the hydrophobic portion of the interior surface; emitting, using at least at least one light source, light; transmitting the light through the hydrophobic portion of the interior surface and at least one of the first or third portions without scattering the light; receiving, using at least one lens, the light transmitted through the hydrophobic portion of the interior surface and the at least one of the first or third portions; transmitting, through the at least one lens, the light transmitted through the hydrophobic portion of the interior surface and the at least one of the first or third portions; receiving, using an image sensor, the transmitted light from the at least one lens; generating and transmitting, using the image sensor, data characterizing the transmitted light from the at least one lens; storing computer readable instructions in a memory element; and executing the computer readable instructions, using at least one specially programmed processor and the data, to generate at least one image of the at least one of the first or third portions.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements of the disclosure. It is to be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure.

Figure 1:
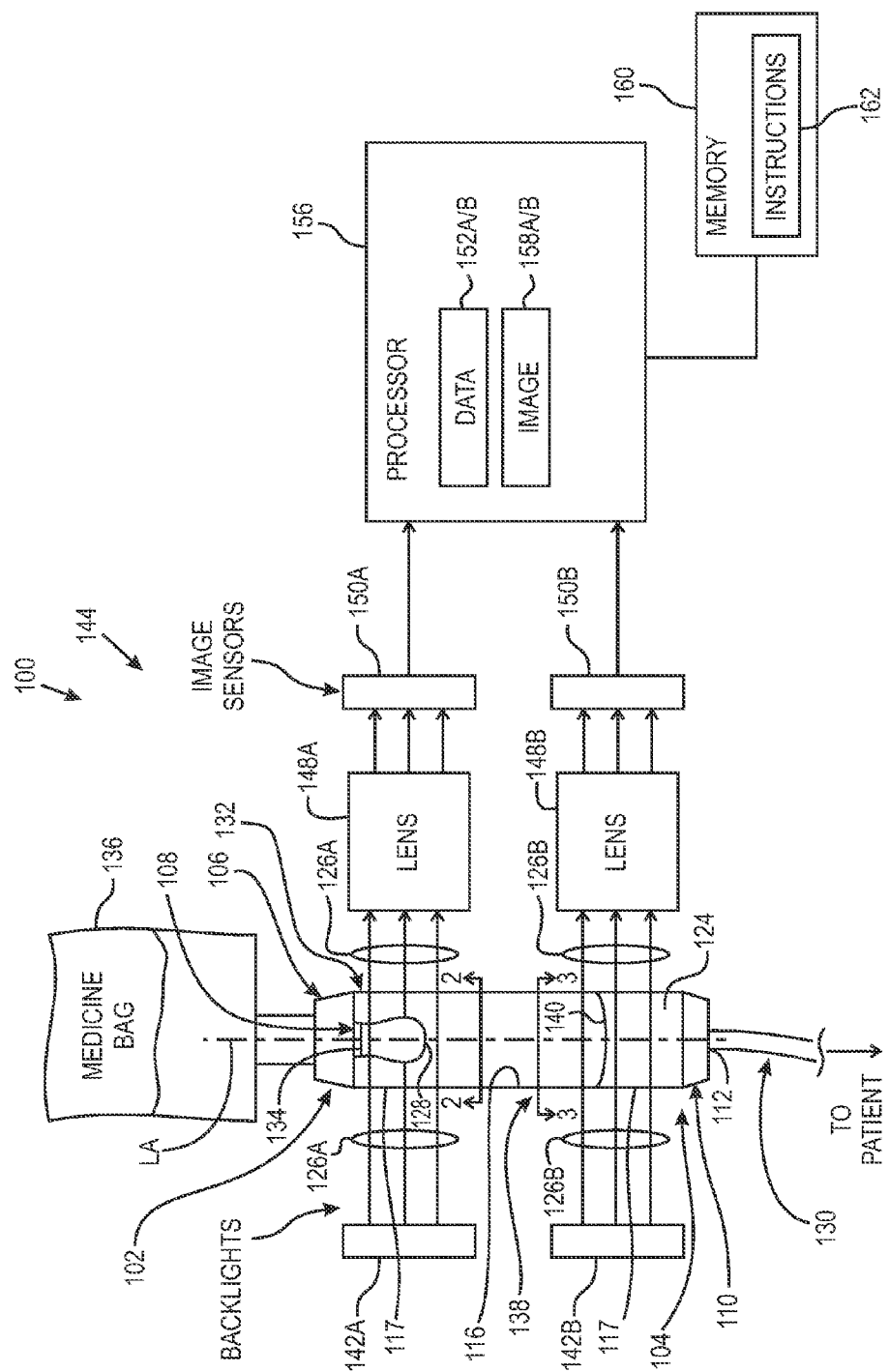
FIG. 1 is a schematic representation of an optical imaging system including a drip chamber with a hydrophobic portion of the interior surface.

FIG. 1 is a schematic representation of optical imaging system 100 including drip chamber 102 with a hydrophobic portion of the interior surface.

Figure 2:
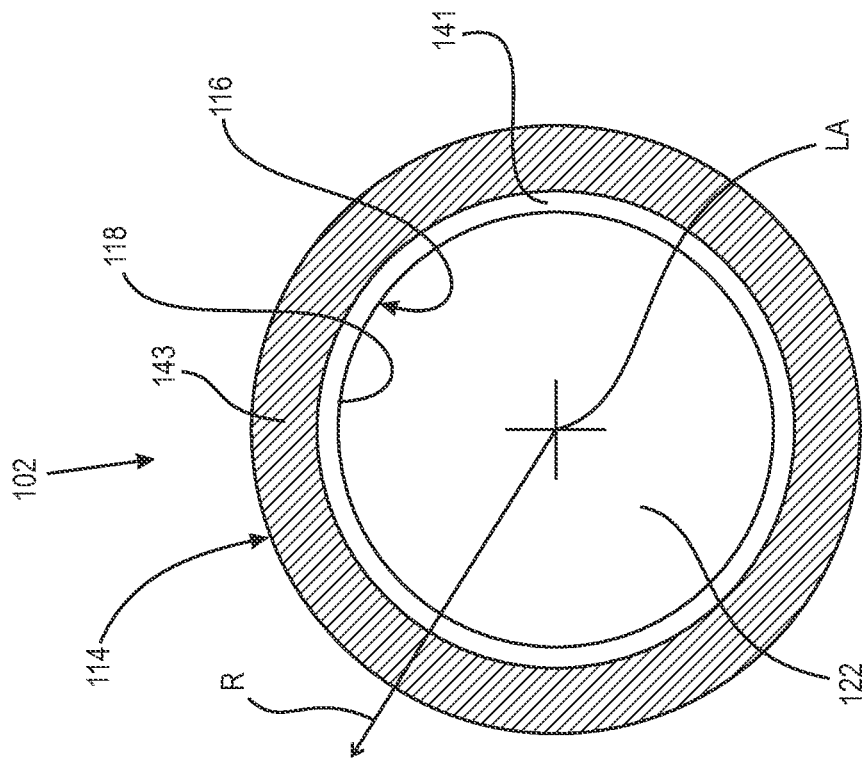
FIG. 2 is a cross-section view generally along line 2-2 in FIG. 1.
Figure 5:
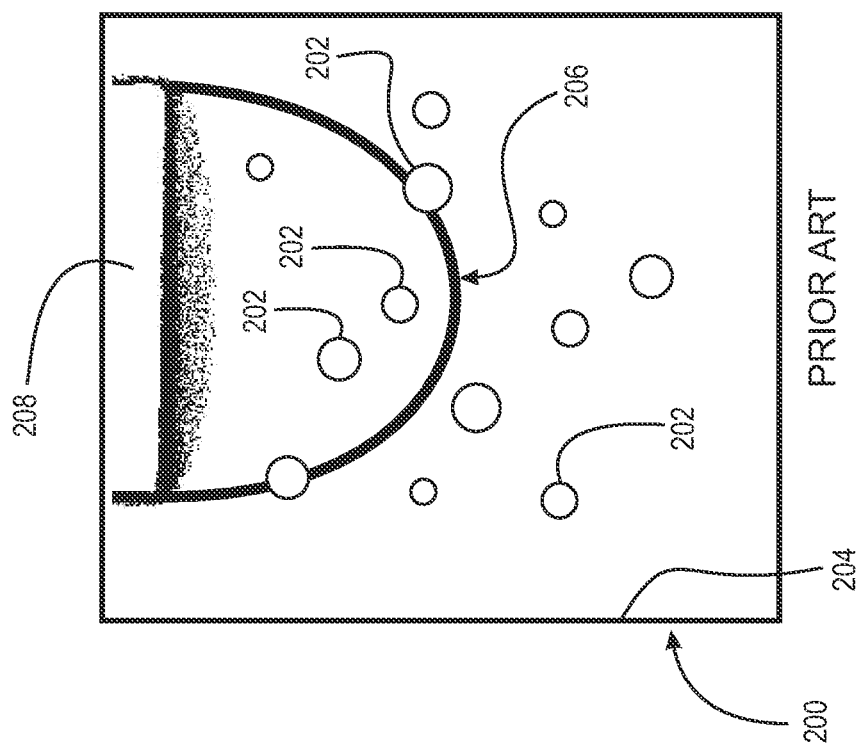

FIG. 2 is a cross-section of drip chamber 102 generally along line 2-2 in FIG. 1.

Figure 3:
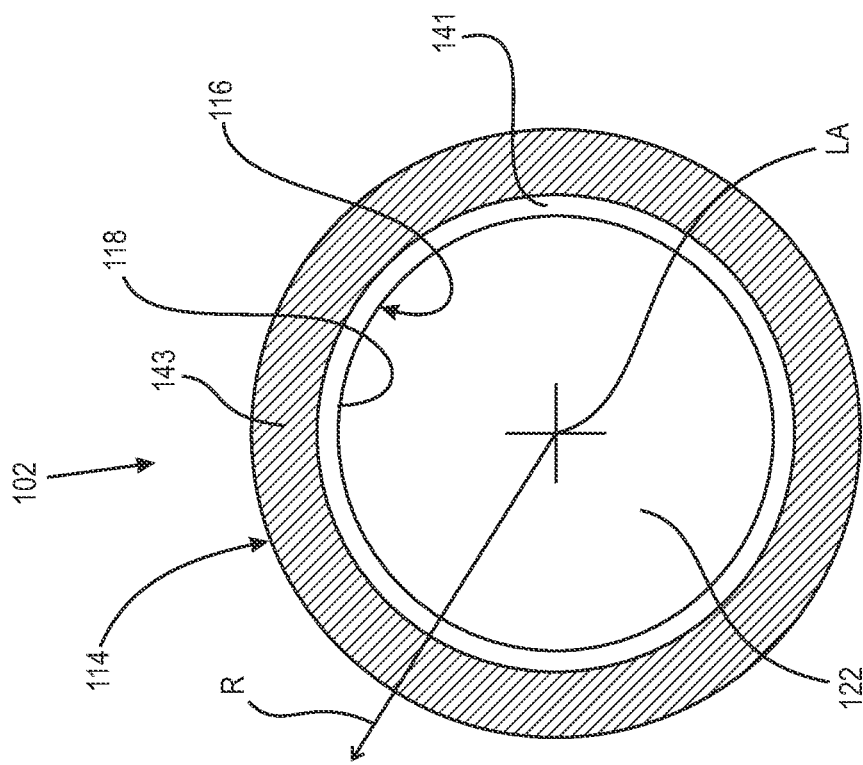
FIG. 3 is a cross-section view generally along line 3-3 in FIG. 1.

FIG. 3 is a cross-section of drip chamber 102 generally along line 3-3 in FIG. 1. The following should be viewed in light of FIGS. 1-3. Drip chamber 102 for infusion tube 104 includes end 106 with drip tube 108 and end 110 including exit port 112. Drip chamber 102 includes wall 114 connecting ends 106 and 110. Wall 114 includes interior surface 116 having at least one hydrophobic portion 118. It should be understood that FIGS. 2 and 3 are not scale drawings and that the thickness of portion 118 in FIGS. 2 and 3 is exaggerated for purposes of illustration. Wall 114 includes space 122 enclosed by interior surface 116 and ends 106 and 110. Hydrophobic portion 118 repels liquid 124 in drip chamber 102. Hydrophobic portion 118 is optically clear and enables light to refract through hydrophobic portion 118 and wall 114 in the same manner as is the case when the hydrophobic portion 118 is not present on interior surface 116, as further described below. Stated otherwise, hydrophobic portion 118 enables direct mapping of light 126A and 126B, passing through portion 118, from a point, such as pendant drop 128 on drip tube 108, within drip chamber 102, to a point on an image (described below) of the point in drip chamber 102. That is, hydrophobic portion 118 enables points illuminated in drip chamber 102 by the emitted light to be accurately imaged using light transmitted through hydrophobic portion 118. In an example embodiment, infusion tube 104 includes output tube 130.

In an example embodiment, hydrophobic portion 118 is aligned with portion 132 of drip chamber 102, including end 106, in direction R orthogonal to longitudinal axis LA for drip chamber 102. Axis LA passes through ends 106 and 110. Portion 132 is sized to include drop 128 pendant from end 134 of drip tube 108. Thus, hydrophobic portion 118 enables accurate optical imaging of pendant drop 128 by preventing the droplets described above from forming on portion 118, while enabling undistorted light transmission. Optical imaging of drop(s) 128 can be used to control flow of liquid 124 through drip chamber 102 or can be used to detect alarm conditions, such as an empty bag alarm for bag 136 supplying liquid 124 to drip chamber 102.

In an example embodiment, hydrophobic portion 118 is aligned with portion 138 of drip chamber 102, between ends 106 and 110, in direction R. In an example embodiment, portion 138 is located to include meniscus 140 for liquid 124 in drip chamber 102. Thus, hydrophobic portion 118 enables accurate optical imaging of meniscus 140 by preventing the droplets described above from forming on portion 118, while enabling undistorted light transmission. Optical imaging of meniscus 140 can be used to determine a level of liquid 124 in chamber 102, which can be used to control flow of liquid 124 through drip chamber 102. In an example embodiment, hydrophobic portion 118 covers both portions 132 and 138. In an example embodiment, hydrophobic portion 118 covers more than portions 132 and 138. In an example embodiment, hydrophobic portion 118 covers the entirety of surface 116 between ends 106 or 110.

In an example embodiment, a contact angle for liquid 124 in contact with hydrophobic portion 118 is between 90 and 180 degrees. As is understood in the art, the contact angle is an angle, measured through liquid, such as liquid 124, where a liquid interface contacts a hydrophobic material, such as hydrophobic portion 118. The angle range described above enables robust repelling of liquid from portion 118.

Figure 4:
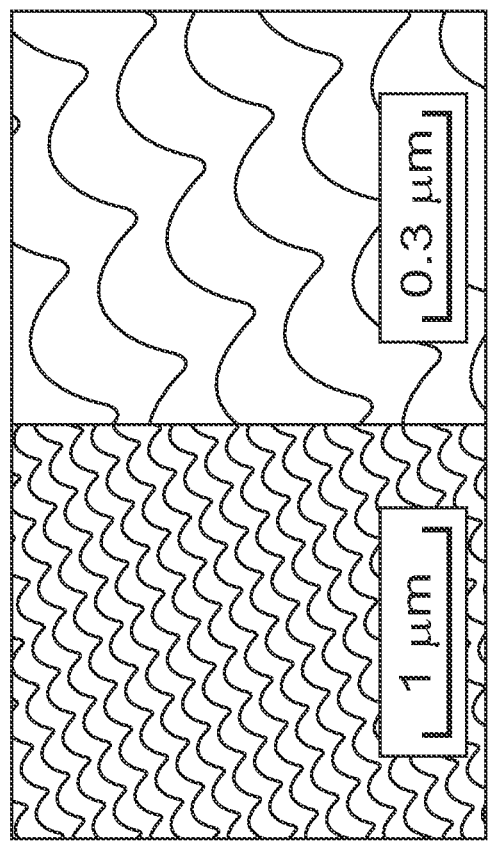
FIG. 4 is a picture illustrating example periodic structure for a hydrophobic portion of the interior surface; and, FIG. 5 is a pictorial representation of a prior art drip chamber with spurious droplets clinging to an interior surface of the drip chamber.

FIG. 4 is a picture illustrating example periodic structure for hydrophobic portion 118. In an example embodiment, hydrophobic portion 118 includes a plurality of periodic structures. In an example embodiment, hydrophobic portion 118 includes a plurality of structures in a non-periodic configuration.

In an example embodiment, hydrophobic portion 118 is formed of a same piece of material forming wall 114, that is, hydrophobic portion 118 is integral to material forming wall 114. For example, interior surface 116 is operated upon in some fashion to create hydrophobic portion 118. As an example, interior surface 116 can be molded using injection molding, injection-compression molding, compression molding, or embossing, to form hydrophobic portion 118. Hydrophobic portion 118 can be formed by modifying surface 116 with surface modification technologies such as plasma.

In an example embodiment, hydrophobic portion 118 is formed of a material 141, separate from material 143 forming wall 114. Material 141 is adhered to material 143. Material 141 can include a polymer, such as, but not limited to acrylic, polystyrene, polycarbonate, vinyl or a mixture of polymers.

In an example embodiment, hydrophobic portion 118 is a coating free of microstructure, such as wax, polytetrafluoroethylene, or water repellent glass powder, applied to surface 116.

In an example embodiment, the material forming hydrophobic portion 118 is fluorinated to improve hydrophobic properties.

In addition to the desirable optical clarity characteristics noted above, in an example embodiment, hydrophobic portion 118 reflects less than one percent of light incident upon hydrophobic portion 118. Thus, the vast majority of light incident upon hydrophobic portion 118 is transmitted through wall 114, enabling high resolution and accurate imagery, and virtually eliminating fresnel reflectance or glare.

In an example embodiment, hydrophobic portion 118 repels: inorganic liquid such as water; organic liquid such as alcohols, proteins, and oils; a solution of an inorganic liquid with a dissolved organic substance; a solution of an inorganic liquid with a dissolved inorganic substance; a solution of an organic liquid with a dissolved organic substance; and, a solution of an organic liquid with a dissolved inorganic substance.

The following provides further exemplary detail regarding hydrophobic portion 118. Hydrophobic portion 118 can be a one-dimensional or a two-dimensional array of microstructure. Hydrophobic portion 118 can have random or stochastic structure. The depth of hydrophobic portion 118 can be between 50 nm and 500 nm. The pitch of an array of hydrophobic microstructure for hydrophobic portion 118 can be between 50 nm and 500 nm.

In an example embodiment, when hydrophobic portion 118 is microstructured, the microstructure can have a cross-sectional profile that is substantially triangular, partially elliptical, parabolic, or hair-like with an indeterminate profile. In an example embodiment, surface 116 is transparent to light 126A and 126B, but is tinted for visual differentiation by the naked eye. In an example embodiment, the microstructure is oriented substantially orthogonal to wall 114. In an example, the microstructure is oriented at an acute angle with respect to wall 114, for example, angled toward end 106 or toward end 110.

As shown in FIG. 1, optical imaging system 100 can be used with infusion tube 104 including drip chamber 102. In an example embodiment, system 100 includes at least one light source 142, for example sources 142A and 142B for emitting light 126A and 126B, respectively, and system 100 includes optics system 144. System 144 includes at least one lens 148, for example, lenses 148A and 148B, and at least one image sensor 150, for example, sensors 150A and 150B. Lenses 148A and 148B are for receiving and transmitting light 126A and 126B transmitted through hydrophobic portion 118 of the interior surface and portions 132 and 138, respectively. Sensors 150A and 150B receive the transmitted light 126A and 126B from lenses 148A and 148B, respectively, and generate and transmit data 152A and 152B characterizing transmitted light 126A and 126B from lenses 148A and 148B, respectively. System 100 includes at least one specially programmed processor 156 configured to generate images 158A and 158B of portions 132 and 138, respectively. System 100 includes memory element 160 configured to store computer executable instructions 162. Processor 156 is configured to execute instructions 162 to generate images 158A and 158B. Note that system can include only light source 142A, lens 148A, and sensor 150A, and not light source 142B, lens 148B, and sensor 150B, or light source 142B, lens 148B, and sensor 150B and not light source 142A, lens 148A, and sensor 150A.

As noted above, image 158A can include pendant drop 128 and image 158A can be used to control flow through infusion tube 102 or to monitor for alarm conditions. As noted above, image 158B can include meniscus 140 and image 158B can be used to monitor the level of meniscus 140 in drip chamber 102.

Advantageously, hydrophobic portion 118 enables more accurate and precise images 158A and 158B by eliminating spurious droplets, noted above, clinging to interior surface 116, while enabling diffused light transmission. For example, a rendering of pendant drop 128 in image 158A is not cluttered or obscured by spurious droplets clinging to surface 116 in portion 130, while at the same time benefiting from diffused transmission of the light used to form image 158A. For example, the boundary of meniscus 140 is not obscured or distorted by spurious droplets clinging to surface 116 in portion 138 between meniscus 140 and portion 130, while at the same time benefiting from diffused transmission of the light used to form image 158B.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A drip chamber for an infusion tube, comprising:
   a first end including a drip tube;
   a second end including an exit port;
   a wall extending between the first end and the second end, the wall having an interior surface including a hydrophobic portion, and having a space defined by the interior surface of the wall and the first and second ends; and
   the hydrophobic portion configured for refracting substantially all light being transmitted through the wall, and eliminating substantially all reflectance or glare formed on the wall;
   wherein the hydrophobic portion of the interior surface repels liquid contacting the hydrophobic portion; and,
   the hydrophobic portion of the interior surface enables the light to refract through the hydrophobic portion and the wall in the same manner as is the case when the hydrophobic portion is not present on the interior surface.

2. The drip chamber of claim 1, wherein the hydrophobic portion of the interior surface enables direct mapping of the light passing through the hydrophobic portion of the interior surface from a point within the drip chamber to a point on an image of the point in the drip chamber.

3. The drip chamber of claim 1, wherein the hydrophobic portion of the interior surface is aligned with the end of the drip tube in a direction orthogonal to a longitudinal axis for the drip chamber passing through the first and second ends of the drip chamber.

4. The drip chamber of claim 1, wherein when the drip chamber includes fluid disposed in the drip chamber, the hydrophobic portion of the interior surface is aligned with a meniscus for the fluid in a direction orthogonal to a longitudinal axis for the drip chamber passing through the first and second ends of the drip chamber.

5. The drip chamber of claim 1, wherein:
   a contact angle for a liquid in contact with the hydrophobic portion of the interior surface is between 90 and 180 degrees; and,
   the contact angle is an angle, measured through the liquid, where a liquid interface contacts the hydrophobic portion of the interior surface.

6. The drip chamber of claim 1, wherein the hydrophobic portion of the interior surface includes a first plurality of periodic structures.

7. The drip chamber of claim 1, wherein the hydrophobic portion of the interior surface includes a first plurality of structures in a non-periodic configuration.

8. The drip chamber of claim 1, wherein the hydrophobic portion of the interior surface is formed of a same piece of material forming the wall.

9. The drip chamber of claim 1, wherein:
   the hydrophobic portion of the interior surface is formed of a first material, separate from a second material forming the wall; and,
   the first material is adhered to the second material.

10. The drip chamber of claim 1, wherein the hydrophobic portion of the interior surface reflects less than one tenth of one percent of light incident upon the hydrophobic portion of the interior surface.

11. The drip chamber of claim 1, wherein the hydrophobic portion of the interior surface repels:
   a first inorganic liquid including water;
   a first organic liquid including alcohols, proteins, or oils;
   a solution of a second inorganic liquid with a dissolved first inorganic substance;
   a solution of a third inorganic liquid with a dissolved first organic substance;

a solution of a second organic liquid with a dissolved second inorganic substance; or, a solution of a third organic liquid with a dissolved second organic substance.

* * * * *